United States Patent
Kiser et al.

(10) Patent No.: US 6,721,586 B2
(45) Date of Patent: Apr. 13, 2004

(54) PERCUTANEOUS BIOLOGICAL FLUID SAMPLING AND ANALYTE MEASUREMENT DEVICES AND METHODS

(75) Inventors: Ernest Kiser, Los Altos, CA (US); Koon-wah Leong, Sunnyvale, CA (US)

(73) Assignee: LifeScan, Inc., Milpitas, CA (US)

( * ) Notice: Subject to any disclaimer, the term of this patent is extended or adjusted under 35 U.S.C. 154(b) by 290 days.

(21) Appl. No.: 09/878,821

(22) Filed: Jun. 12, 2001

(65) Prior Publication Data

US 2002/0188184 A1 Dec. 12, 2002

(51) Int. Cl.$^7$ ................................................. A61B 5/05
(52) U.S. Cl. ........................................ 600/345; 600/573
(58) Field of Search ............................... 600/345, 347, 600/365, 372, 573, 583, 584; 204/403.11, 403.13, 403.14, 403.01; 205/775, 775.5

(56) References Cited

U.S. PATENT DOCUMENTS

| | | |
|---|---|---|
| 5,161,532 A | 11/1992 | Joseph |
| 5,582,184 A | 12/1996 | Erickson et al. |
| 5,746,217 A | 5/1998 | Erickson et al. |
| 5,879,310 A | 3/1999 | Sopp et al. |
| 5,879,367 A | 3/1999 | Latterell et al. |
| 5,942,102 A | 8/1999 | Hodges et al. |
| 6,080,116 A | 6/2000 | Erickson et al. |
| 6,083,196 A | 7/2000 | Trautman et al. |
| 6,091,975 A | 7/2000 | Daddona et al. |
| 6,104,940 A * | 8/2000 | Watanabe et al. ........... 600/345 |
| 6,143,164 A * | 11/2000 | Heller et al. ................ 600/583 |
| 6,162,611 A | 12/2000 | Heller et al. |
| 6,379,324 B1 | 4/2002 | Gartstein et al. |
| 6,501,976 B1 | 12/2002 | Sohrab |

FOREIGN PATENT DOCUMENTS

| | | |
|---|---|---|
| WO | WO97/00441 | 1/1997 |
| WO | WO97/42888 | 11/1997 |
| WO | WO98/00193 | 1/1998 |
| WO | WO908/34541 | 8/1998 |
| WO | WO99/13336 | 3/1999 |
| WO | WO99/27852 | 6/1999 |
| WO | WO99/64580 | 12/1999 |
| WO | WO00/35530 | 6/2000 |
| WO | WO00/45708 | 8/2000 |
| WO | WO00/57177 | 9/2000 |
| WO | WO00/74763 | 12/2000 |
| WO | WO00/74765 | 12/2000 |

* cited by examiner

Primary Examiner—Willis R. Wolfe
(74) Attorney, Agent, or Firm—Carol M. LaSalle; Bozicevic, Field & Francis, LLP (57) ABSTRACT

A device for sampling a biological fluid and measuring at least one target constituent within the biological fluid. The device has at least one electrochemical cell having an inner electrode and an outer electrode in a concentrically-spaced relationship. In a preferred embodiment, the outer electrode has a cylindrical configuration having an open distal end and the inner electrode has an elongated configuration positioned coaxially within the outer electrode and a distal end configured to penetrate the skin. The spacing between the electrodes exerts a capillary force on biological fluid present at the open distal end of the outer electrode. A system is also provided which includes a control unit in electrical communication with the electrochemical cell for controlling the selection and measurement of the target constituent. Methods of sampling of biological fluids within the skin and measuring the sampled fluids are also provided, as well as kits comprising one or more of the inventive devices and/or systems.

46 Claims, 2 Drawing Sheets

PERCUTANEOUS BIOLOGICAL FLUID SAMPLING AND ANALYTE MEASUREMENT DEVICES AND METHODS

FIELD OF THE INVENTION

This invention is related to percutaneous biological fluid sampling and analyte measurement devices and methods.

BACKGROUND OF THE INVENTION

The detection of analytes in biological fluids is of ever increasing importance. Analyte detection assays find use in a variety of applications, including clinical laboratory testing, home testing, etc., where the results of such testing play a prominent role in the diagnosis and management of a variety of disease conditions. Common analytes of interest include glucose, e.g., for diabetes management, cholesterol, and the like.

A common technique for collecting a sample of blood for analyte determination is to pierce the skin at least into the subcutaneous layer to access the underlining blood vessels in order to produce localized bleeding on the body surface. The accessed blood is then collected into a small tube for delivery and analyzed by testing equipment, often in the form of a hand-held instrument having a reagent test strip onto which the blood sample is placed. The fingertip is the most frequently used site for this method of blood collection due to the large number of small blood vessels located therein. This method has the significant disadvantage of being very painful because subcutaneous tissue of the fingertip has a large concentration of nerve endings. It is not uncommon for patients who require frequent monitoring of an analyte to avoid having their blood sampled. With diabetics, for example, the failure to frequently measure their glucose level on a prescribed basis results in a lack of information necessary to properly control the level of glucose. Uncontrolled glucose levels can be very dangerous and even life-threatening. This technique of blood sampling also runs the risk of infection and the transmission of disease to the patient, particularly when done on a high-frequency basis. The problems with this technique are exacerbated by the fact that there is a limited amount of skin surface that can be used for the frequent sampling of blood without forming thick calluses.

To overcome the disadvantages of the above technique and others that are associated with a high degree of pain, certain analyte detection protocols and devices have been developed that use micro-needles or analogous structures to access the interstitial fluid within the skin. The micro-needles are penetrated into the skin to a depth less than the subcutaneous layer so as to minimize the pain felt by the patient. The interstitial fluid is then sampled and tested to determine the concentration of the target constituent. The concentration of a constituent within the interstitial fluid is representative of the concentration of that constituent in other bodily fluids, such as blood.

Conventional micro-needle sampling systems have a drawback in that, because the interstitial fluid inside the human body is at a negative pressure of about 6 mm/Hg, some kind of mechanical or vacuum means is often used in conjunction with the micro-piercing members.

For example, International Patent Application WO 99/27852 discloses the use of vacuum pressure and/or heat to increase the availability of interstitial fluid at the area of skin in which the vacuum or heat is applied. The vacuum pressure causes the portion of skin in the vicinity of the vacuum to become stretched and engorged with interstitial fluid, facilitating the extraction of fluid upon entry into the skin. Another method is disclosed wherein a localized heating element is positioned above the skin, causing interstitial fluid to flow more rapidly at that location, thereby allowing more interstitial fluid to be collected per given unit to time.

Still other detection devices have been developed which avoid penetration of the skin altogether. Instead the outermost layer of skin, called the stratum corneum, is "disrupted" by a more passive means to provide access to or extraction of biological fluid within the skin. Such means includes the use of oscillation energy, the application of chemical reagents to the skin surface, etc. For example, International Patent Application WO 98/34541 discloses the use of an oscillation concentrator, such as a needle or wire, which is positioned at a distance from the skin surface and caused to vibrate by means of an electro-mechanical transducer. The needle is immersed in a receptacle containing a liquid medium placed in contact with the skin. The mechanical vibration of the needle is transferred to the liquid, creating hydrodynamic stress on the skin surface sufficient to disrupt the cellular structure of the stratum corneum. International Patent Applications WO 97/42888 and WO 98/00193 also disclose methods of interstitial fluid detection using ultrasonic vibration.

Thus, despite the work that has already been done in the area of analyte testing, there is a continued interest in the identification of new analyte detection methods that more readily meet the needs of the relevant market. Of particular interest would be the development of a minimally invasive analyte detection system that is practical, manufacturable, accurate and easy to use, as well as safe and efficacious.

Relevant Literature

U.S. Pat. Nos. of interest include: 5,582,184, 5,746,217, 5,820,570, 5,942,102, 6,091,975 and 6,162,611. Other patent documents and publications of interest include: WO 97/00441, WO 97/42888, WO 98/00193 WO 98/34541, WO 99/13336, WO 99/27852, WO 99/64580, WO 00/35530, WO 00/57177 and WO 00/74765A1.

SUMMARY OF THE INVENTION

Minimally invasive biological fluid sampling and analyte measurement devices and systems, as well as methods for using the same, are provided.

Generally, the subject devices of the present invention include an electrochemical cell having spaced-apart outer and inner electrodes for measuring the concentration of analyte within the biological fluid. The outer electrode has a chamber-defining configuration having an open distal end and at least a partially open proximal end. More specifically and preferably, the outer electrode has a continuous wall configuration which defines an interior lumen or chamber having a length. The distal edge of the wall defines a skin-contacting surface or pressure surface. In a preferred embodiment, the outer electrode has a cylindrical configuration defining an annular skin-contacting surface at the distal end such that, when operatively applied to the skin, the annular surface acts as a pressure ring on the skin surface.

The inner electrode has a solid, elongated configuration having a length which is positioned co-axially within the lumen or chamber of the outer electrode. The inner electrode has a proximal end and a distal end configured to pierce a skin surface to provide access to biological fluid. The length of the inner electrode relative to the outer electrode is a factor in determining the depth of penetration of the inner electrode. The outer and inner electrodes may be configured such that their respective distal ends are even with each other, or they may have different distally extending lengths.

The spacing between the electrodes defines a reaction chamber or zone within the electrochemical cell. This spacing is sufficiently narrow to exert a capillary force on the accessed biological fluid at it is open distal end thereby wicking it into the reaction chamber. The electrochemical cell of the present invention may further include an insulator positioned within the reaction chamber in sealed engagement at the proximal end of the electrochemical cell. Collectively, these components define a sensor device having a cup-like configuration.

The sensor device of the present invention is employed to make an electrochemical measurement of an analyte in a sample of biological fluid that has been accessed by the skin-piercing, inner electrode and then transported (by a capillary action) into the electrochemical cell. The electrochemical cell may be designed to provide a coulometric, amperometric or potentiometric measurement. Also, a plurality of the sensor devices of the present invention may be provided in the form of an array. The plurality of sensor devices may have identical configurations, electrode lengths and reagent types, or may have different configurations, electrode lengths and reagent types for accessing different layers of skin and testing different analytes.

An exemplary method of the subject invention involves using at least one subject sensor device just described. The distal end of the device is positioned or cupped over an area of the patient's skin such that the skin-contacting surface of the outer electrode is flush with the skin surface. Slight pressure is exerted on the proximal end of the sensor device, causing the skin-contacting surface to exert a pressure on the contacted skin and thereby causing the covered portion of skin to bulge upward into the spacing between the electrodes. The skin-piercing inner electrode is then able to atraumatically penetrate the skin to a selected depth, preferably to a depth that avoids contacting nerve endings and blood vessels. Next, the sample of biological fluid present at the open distal end of the device is then wicked, by means of a capillary force, into the electrochemical cell. An electrochemical measurement is then made between the electrodes which provides an electrical signal representative of the concentration of the target constituent(s) within the sample. The concentration of the constituent(s) in the patient's blood is then derived from the obtained electrical signal.

A redox reagent system or material may be used within the electrochemical cell to facilitate targeting the analyte(s) of interest. The particular redox reagent material used is selected based on the analyte targeted for measurement.

The subject sensor devices may function as a part of an analyte sensing system that includes a means for controlling the sensor device. Specifically, a control unit is provided in which the control means is electrically coupled with the sensor device and functions to generate and send input signals to the electrochemical cell and to receive output signals from the cell. These functions, among others, are performed by a software algorithm programmed within the control unit that automatically calculates and determines the concentration of the target analyte in the biological sample upon receipt of an output signal from the electrochemical cell. The control unit may further include a display unit for displaying a numerical value representing the analyte concentration.

In operation, one of the electrodes of the electrochemical cell is used as the reference electrode by which an input reference signal is provided to the sensor from a signal generating means. Preferably, the inner electrode functions as a reference electrode for receiving an electrical signal from a signal-generating source, e.g., the control unit. The outer electrode then functions as a working electrode that provides an output signal from the electrochemical cell to a signal-receiving means, e.g., the control unit. This output signal represents the concentration of the target analyte within the sampled fluid.

An exemplary method of the subject invention involves using at least one subject sensor device. The sensor device is positioned over a target area of skin, and with sufficient pressure, the inner electrode/lancing member is caused to penetrate the surface of the skin to a selected depth, preferably to a depth that avoids contacting nerve endings and blood vessels. Next, the sample of biological fluid present at the open distal end of the sensor device is then wicked into the spacing or reaction zone between the inner and outer electrodes by capillary force. An electrochemical measurement is then made between the working and reference electrodes that provides an electrical signal that is representative of the concentration the constituent in the sample. The concentration of the constituent(s) in the patient's blood is then derived from the obtained electrical signal. A numerical value representing this concentration may then be displayed on a display unit. A software algorithm that is part of the device, e.g., programmed into a control unit present in the device, may be employed to determine the signal levels transmitted by the control unit to the cell and for deriving the concentration level of the target analyte.

BRIEF DESCRIPTION OF THE DRAWINGS

FIG. 1 includes FIGS. 1A and 1B wherein

FIG. 2 includes FIGS. 2A and 2B wherein

DETAILED DESCRIPTION OF THE PREFERED EMBODIMENTS

The present invention finds use in the sampling of biological fluids, such as blood and interstitial fluid, and in the detection and measurement of a variety of different constituents, e.g., glucose, cholesterol, electrolytes, pharmaceuticals, illicit drugs, and the like within the biological fluid. The present invention is especially well-suited for the sampling of interstitial fluid and the measuring of the concentration of glucose therein.

In general, the subject devices include an electrochemical cell and a skin-piercing means in the form of one of the electrodes of the electrochemical cell. The electrochemical cell has a configuration for exerting a capillary force on biological fluid exposed to it. Preferably these components are integrated into a single structure.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a test strip" includes a plurality of such test strips and reference to "the processor" includes reference to one or more processors and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

EXEMPLARY EMBODIMENTS OF THE SENSOR DEVICES

Generally, the sensor devices of the present invention include an electrochemical cell having an electrode arrangement of a reference electrode and a working electrode. The two electrodes are in a spaced-apart relationship such that a surface of one electrode faces a surface of the other electrode. The space between the two electrodes defines a reaction chamber or zone into which sampled biological fluid is transferred and is tested for the concentration of a targeted analyte. The reference electrode provides an input signal to the electrochemical cell, and the working electrode provides an output signal representative of the analyte concentration of the sampled biological fluid that is transferred to within the electrochemical cell.

The general configuration of exemplary sensor devices of the present invention will now be described with reference to FIGS. 1 and 2. FIGS. 1A, 1B and 2A, 2B illustrate sensor devices 100 and 200, respectively, having a cup-like configuration that has a substantially circular top view, best seen in FIGS. 1B and 2B. However, any suitable cross-sectional configuration may be employed including, but not limited to other annular shapes such as elliptical or oblong, or polygonal configurations, such as square and rectangular.

The electrochemical cells are defined by a first or outer electrode 102, 202, respectively, a second or inner electrode 104, 204, respectively, having a concentric relationship, which may also be described as circumferential or co-axial. Here, the outer electrodes 102, 202 function as the working electrode and the inner electrodes 104, 204 function as the reference or counter electrode. The respective electrochemical cells further include an insulating material 106, 206, respectively, concentrically positioned between the respective electrode pairs.

Here, first or outer electrode 102, 202 has a substantially cylindrical configuration in the form of a substantially cylindrical wall having a proximal end 114 and 214, respectively, and a distal end 116 and 216, respectively. Electrodes 102 and 202, respectively, preferably have blunt distal edges or skin-contacting surfaces 118 and 218, respectively, to provide a pressure surface or ring when operatively placed against the skin surface. At the proximal end 114 of outer electrode 102 is an inwardly extending base portion 112 that at least partially defines a proximal or top cover portion when device 100 is operatively inserted into the patient's skin. On the other hand, the cylindrical wall of outer electrode 202 defines an open lumen extending from a proximal end 214 to a distal end 216.

Second or inner electrodes 104 and 204 each have a distal end 108 and 208, respectively, a proximal end 110 and 210, respectively, and an elongated configuration therebetween which is positioned co-axially within the walls of first or outer electrodes 102 and 202, respectively. The spacing between the respective inner and outer electrodes define a reaction chamber or zone 120, 220 wherein the sampled biological fluid is collected for electrochemical measurement.

Distal ends 108, 208 of inner electrodes 104 and 204, respectively, have a sharp tip in the form of a lancing member. Alternatively, the lancing member may be a separate component mounted to the distal end of the inner electrode. In either configuration, the lancing member has a beveled or sliced configuration, as shown in FIGS. 1A and 2A, respectively, to more easily penetrate the skin when pressure is exerted on the respective devices 100 and 200.

Distal ends 108, 208 may extend a length that is even with the distal ends 116, 216 of outer electrodes 102 and 202, respectively. However, distal ends 108 and 208 may be slightly shorter or longer than the distal ends 116, 216 of outer electrodes 102 and 202, respectively, depending on the desired length of penetration of second electrodes 104 and 204. For example, if it is desired to penetrate a relatively shallow depth, not beyond the epidermis for example, inner electrodes 104, 204 may be slightly shorter than outer electrodes 102, 202, respectively. If, however, it is desired to penetrate a relatively deeper depth, not beyond the dermis layer for example, inner electrode 104, 204 may be slightly longer than outer electrode 102, 202, respectively. Proximal ends 110 and 210 of inner electrodes 104 and 204, respectively, extend a short distance proximally of the distal ends 114 and 214 of outer electrodes 102 and 202, respectively, to provide a conductive contact point to a source of electrical energy (not shown).

The subject inner electrodes 104, 204 are configured to be mechanically stable and strong enough to penetrate the stratum corneum without breaking or flexing. Preferably, they are made of a biocompatible material so as not to cause irritation to the skin or an undesirable tissue response. Suitable metallic materials include stainless steel, titanium, precious metals or alloys thereof.

Sandwiched between the facing surfaces of the inner and outer electrodes pairs is an insulating material or insulator 106 and 206, respectively, for electrically isolating the inner and outer electrodes from each other, and for sealing the proximal end of the sensor device. In sensor device 100 of FIG. 1, insulator 106 takes the form of an annular ring (but may take other forms depending on the configurations of the electrodes) positioned externally to proximal end 110 of inner electrode 104 and internal to base portion 112 of outer electrode 102. In sensor device 200 of FIG. 2, insulator 206 is also in the form of an annular ring (but may take other forms depending on the configurations of the electrodes) positioned externally to proximal end 210 of inner electrode 204 and internal to distal end 214 of outer electrode 102.

The insulator may be formed of or coated with an insulating material, such as a ceramic, glass, silica, polymer or plastics. Examples of ceramics are aluminum oxide, silicon carbide and zirconium oxide. Examples of polymers are polyacrylates, epoxies, polyesters, polyolefin, polyurethane, polysiloxane, polycyanoacrylate or their composites.

An important aspect of the present invention is to eliminate or at least greatly minimize the pain and bleeding suffered by a patient during the sampling process. Accordingly, the penetration lengths and diameters of inner electrodes 108, 208 must be within certain ranges to accomplish this goal. Of course, those values will vary depending on the type of biological fluid (e.g., interstitial fluid, blood or both) desired for sampling and the thickness of the skin layers of the particular patient being tested.

The skin includes three distinct layers, a top layer called the epidermis, a middle layer called the dermis and a bottom layer called the subcutaneous layer. The epidermis is about 60 to 120 $\mu$m (microns) thick and comprises four distinct layers: a 10 to 20 $\mu$m outer layer, called the stratum comeum, followed by the stratum granulosum, stratum malpighii and stratum germinativum. The stratum comeum contains cells filled with bundles of cross-linked keratin and keratohyalin surrounded by an extracellular matrix of lipids. The inner three layers are collectively referred to as the viable epidermis and have a total thickness in the range of about 50 to 100 $\mu$m. The viable epidermis is responsible for diffusing metabolites to and from the dermis. The epidermis contains no blood cells or nerve endings. The dermis is much thicker than the epidermis, having a thickness in the range from about 2,000 to 3,000 $\mu$m. The dermal layer generally consists of a dense bed of connective tissue, including collagen fibers, and interstitial fluid dispersed throughout these fibers. Below the dermal layer is the subcutaneous tissue that contains the blood capillaries and the majority of nerve endings within the skin.

Thus, the inner electrodes 108, 208 of the present invention preferably have penetration lengths that extend no deeper than the dermis layer when fully penetrated into the skin to minimize the pain felt by the patient, however, they may be longer if necessary for the particular sampling application at hand. In order to effectively and atraumatically penetrate the skin, the length of the inner electrode is generally at least about three times greater than the diameter of the inner electrode, but may be more. The minimum inner electrode diameter is about 75 $\mu$m, dependent upon the strength of the material the inner electrode is made of.

The inner diameter of outer electrodes 102, 202 is generally in the range from about 1000 to 5000 $\mu$m, and typically in the range from about 2000 to 4000 $\mu$m, and more typically in the range from about 2500 to 3500 $\mu$m. Outer electrodes have a thickness in the range from about 100 to 1000 Angstroms, and typically in the range from about 150 to 300 Angstroms. Such a thin layer can be made by vacuum deposition or electroplating the electrode material onto the inner surface of a tubular object having the desirable inside diameter. The wall thickness of the tubular object is in the range of about 2000 to 4000 $\mu$m. Accordingly, the reaction zones 120 and 220, respectively, have volumes generally in the range from about 0.1 to 2 $\mu$L, and typically do not exceed about 1 $\mu$L. Sensor devices 100, 200 are sized and configured such that the spacing between the electrodes is sufficient to provide a capillary force on the biological fluid that emerges from the penetration site in order to transfer an amount of the fluid proximally within the sensor device.

The inner diameter of outer electrodes 102, 202 is generally in the range from about 1000 to 5000 $\mu$m, and typically in the range from about 2000 to 4000 $\mu$m, and more typically in the range from about 2500 to 3500 $\mu$m. Outer electrodes have a thickness in the range from about 100 to 1000 Angstroms, and typically in the range from about 150 to 300 Angstroms. Such a thin layer can be made by vacuum depositon or electroplating the electrode material onto the inner surface of a tubular object having the desirable inside diameter. The wall thickness of the tubular object is in the range of about 2000 to 4000 $\mu$m. Accordingly, the reaction zones 120 and 220, respectively, have volumes generally in the range from about 0.1 to 2 $\mu$L, and typically does not exceed about 1 $\mu$L. Sensor devices 100, 200 are sized and configured such that the spacing between the electrodes is sufficient to provide a capillary force on the biological fluid that emerges from the penetration site in order to transfer an amount of the fluid proximally within the sensor device.

Figure 1A:
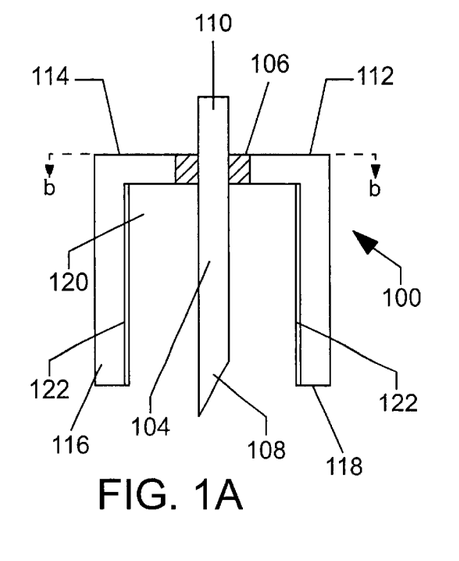
FIG. 1A is a cross-sectional side view of an embodiment of the sensor device of the present invention and FIG. 1B is a top view of the sensor device of FIG. 1A along the arrows b—b.
Figure 1B:
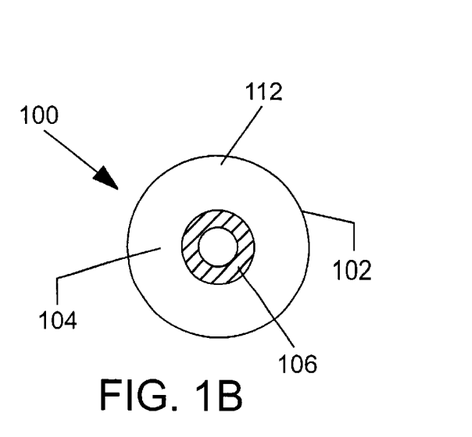
Figure 2A:
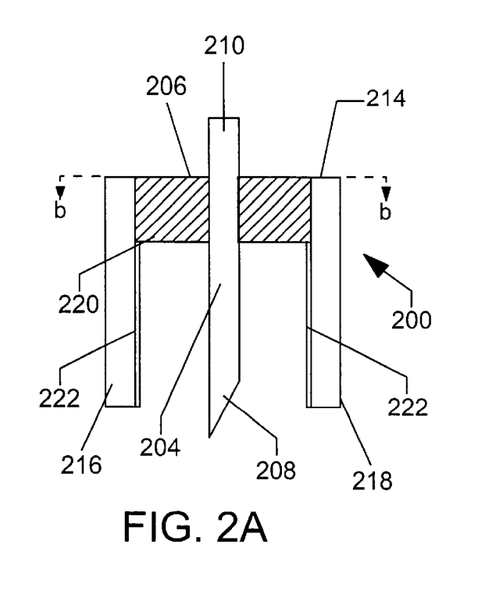
FIG. 2A is a cross-sectional side view of another embodiment of the sensor device of the present invention and FIG. 2B is a top view of the sensor device of FIG. 2A taken along the arrows b—b.
Figure 2B:
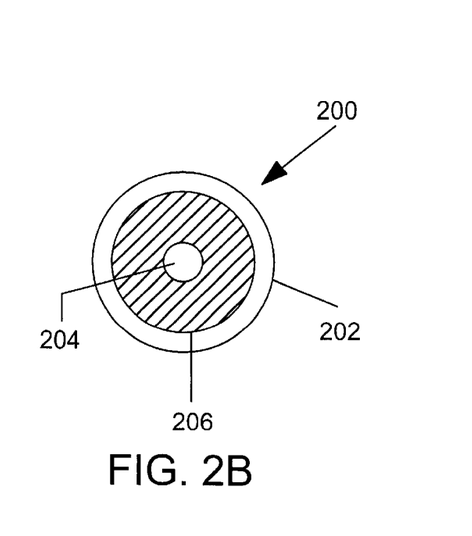

At least the surfaces of the electrodes of FIGS. 1 and 2 that face the reaction zones 120 and 220 of sensor devices 100 and 200, respectively, are comprised of highly conductive metal, such as palladium, gold, platinum, silver, iridium, carbon, doped indium tin oxide, stainless steel and the like, or a combination of such materials. Most typically the metal is gold, platinum or palladium. Although the entire electrode may be made of metal, each electrode can be made up of an inert support or backing substrate on the surface of which is a thin layer of the metal component (e.g., an electroplated metal layer) of the electrode.

A redox reagent system or material 122 and 222 of FIGS. 1 and 2, respectively, may be used within the electrochemical cell to facilitate targeting the analyte(s) of interest. The particular redox reagent material used is selected based on the analyte targeted for measurement. The reagent may be deposited on one or both electrodes, preferably on at least a portion of the electrode surfaces facing the reaction zone. The redox reagent system will be described in more detail below.

While exemplary configurations of electrical chemical cells have been described, various types of electrochemical systems and methods commonly known in the art of analyte detection and measurement may be employed by the present invention, including systems that are amperometric (i.e., measure current), coulometric (i.e., measure electrical charge) or potentiometric (i.e., measure voltage). Examples of these types of electrochemical measurement systems are further described in U.S. Pat. Nos.: 4,224,125; 4,545,382; and 5,266,179; as well as WO 97/18465 and WO 99/49307; the disclosures of which are herein incorporated by reference.

Reagents

In order to single out and sense the target analyte or constituent selected for analysis over the other constituents in the sampled biological fluid, a redox reagent is typically employed within the reaction zone within the electrochemical cell. The redox reagent material is typically deposited on at least one of the facing surfaces of the two electrodes whereby biological fluid present in the reaction zone chemically reacts with the reagent material. As such, the reagent is preferably coated or deposited on the surface(s) by means of dip coating or inkjet coating. The reagent being used is selected based on the analyte targeted for detection. The interaction of the reagent system and the corresponding constituent or analyte is employed in the electrochemical measurement protocol to determine the concentration of the target analyte or constituent in the cell.

The reagent system present in the reaction area typically includes at least an enzyme(s) and a mediator. In many embodiments, the enzyme member(s) of the reagent system is an enzyme or a plurality of enzymes that work in concert to oxidize the analyte of interest. In other words, the enzyme component of the reagent system is made up of a single analyte oxidizing enzyme or a collection of two or more enzymes that work in concert to oxidize the analyte of interest. Enzymes of interest include oxidases, dehydrogenases, lipases, kinases, diaphorases, quinoproteins and the like. The specific enzyme present in the reaction area depends on the particular analyte for which the electrochemical test strip is designed to detect, where representative enzymes include: glucose oxidase, glucose dehydrogenase, cholesterol esterase, cholesterol oxidase, lipoprotein lipase, glycerol kinase, glycerol-3-phosphate oxidase, lactate oxidase, lactate dehydrogenase, pyruvate oxidase, alcohol oxidase, bilirubin oxidase, uricase, and the like. In many preferred embodiments where the analyte of interest is glucose, the enzyme component of the reagent system is a glucose-oxidizing enzyme (e.g., a glucose oxidase or glucose dehydrogenase).

The second component of the reagent system is a mediator component, which is made up of one or more mediator agents. A variety of different mediator agents are known in the art and include: ferricyanide, phenazine ethosulphate, phenazine methosulfate, pheylenediamine, 1-methoxyphenazine methosulfate, 2,6-dimethyl-1,4-benzoquinone,2, 5-dichloro-1,4-benzoquinone, ferrocene derivatives, osmium bipyridyl complexes, ruthenium complexes and the like. In those embodiments where glucose is the analyte of interest and either glucose oxidase or glucose dehydrogenase is the enzyme component, the mediator of particular interest is ferricyanide. Other reagents that may be present in the reaction area include buffering agents, (e.g., citraconate, citrate, phosphate), "Good" buffers and the like.

The reagent is generally present in dry form. The amounts of the various components may vary wherein the amount of enzyme component typically ranges from about 0.1 to 10% by weight.

The Sensor System

In the sensor system of the present invention, the reference and working electrodes of the electrochemical cell are in electrical communication with a control means that sets the input reference signal transmitted to the electrochemical cell, receives the output signal from the electrochemical cell and then derives the concentration level of the analyte within the sample from the output signal. In other words the control means provides a means for applying an electrical current between the two electrodes, measuring a change in the current over time and relating the observed change in current to the concentration of analyte present in the electrochemical cell. The concentration of the analyte in the patient's blood is then derived from the concentration level in the fluid sample, the numerical value of which is preferably provided as an output signal to a display means.

Figure 3:
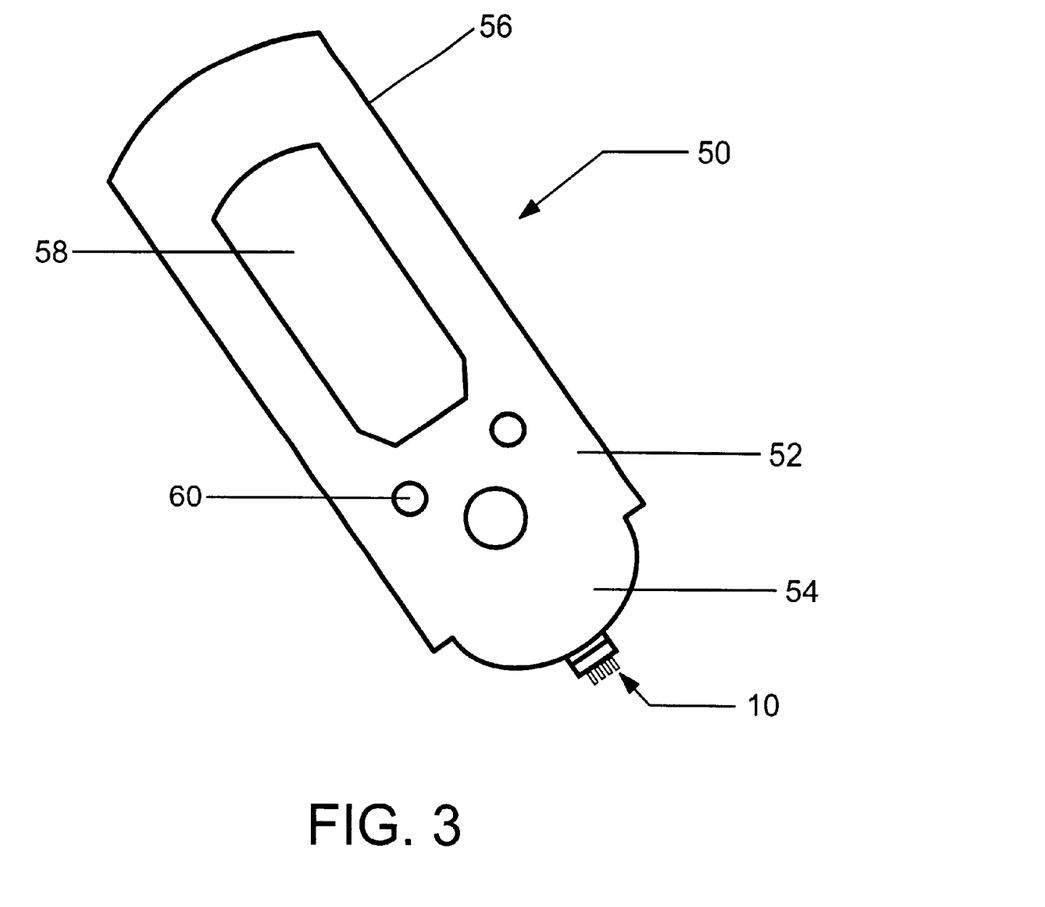
FIG. 3 is a schematic representation of a sensor device of the present invention operatively mounted to a control unit of the present invention.

Preferably, the control and display means are integrally housed within a hand-held control unit such as that illustrated in FIG. 3. The control unit preferably also provides a means of securing or holding one or more sensor devices or an array of sensor devices in a position and arrangement suitable for the particular sampling and measuring application at hand.

Referring now to FIG. 3, there is shown a schematic representation of a sensor system 50 of the subject invention. Sensor system 50 comprises a hand-held control unit 52 and a sensor device 10, such as sensor devices 100 and 200 discussed above, operatively mounted to distal end 54 of control unit 52. Control unit 52 has a housing 56, preferably made of a medical grade plastic material, having a low-profile configuration which houses a means (not shown) for controlling the measurement means of sensor device 10, i.e., generating and transmitting input reference signals to the electrochemical cell of sensor device 10 and receiving output measurement signals from the cell. A software algorithm programmed within control unit 52 automatically calculates and determines the concentration of the target analyte in the biological sample upon receipt of the output signal. The concentration level (among other desired information) is then transmitted to an external display means or screen 58 that displays information to the user. Control interface buttons 60 are provided to allow the user to input information, such as the type of analyte targeted for measurement, to the control means.

Sensor device 10 is electrically and physically coupled to control unit 52. Electrical communication between the two is established by means of conductive contacts (not shown) on device 10 and corresponding electrical traces (not shown) within control unit 52. Preferably, device 10 and control unit 52 are physically coupled by a quick lock-and-release mechanism (many of which are commonly known) such that a used sensor device can be easily removed and replaced. Control unit 52 is preferably reusable and usable with any number of sensor devices of the subject invention. These features facilitate the taking of multiple samples and measurements in an efficient and rapid manner.

Any suitable number of sensor devices, in the form of an array, may be employed by the present invention. The array may be provided on a support means such as a substrate that is electrically and physically engageable with control unit 52. The number of sensor devices employed will depend upon various factors including the agent being detected, the body surface location into which the sensor devices are inserted, the sample site, the fluid volume and the like. The sensor device array may comprise inner electrodes/lancing members having varying shapes, lengths, widths and tip configurations.

Methods of Use

Also provided by the subject invention are methods for using the subject devices and sensor systems to determine the concentration of an analyte in a physiological sample. A variety of different analytes may be detected using the subject sensor systems, where representative analytes include glucose, cholesterol, lactate, alcohol, and the like.

In practicing the subject methods (with reference to thes), the first step is to provide a sensor device 10 of the present invention. Preferably, sensor device 10 is particularly configured (i.e., containing the appropriate reagent) for targeting the analyte(s) of interest. The sensor device 10 is operatively engaged and interfaced with a control unit 52 that can be manually held and controlled by the user. Control unit 52 is programmed for testing the targeted analyte(s).

The user positions sensor device 10 over a selected area of the patient's skin such that the distal edge of the outer electrode, 102 of FIG. 1 and 202 of FIG. 2, is in contact with the skin surface. With slight pressure, the inner electrode or lancing member is caused to penetrate into the skin. The depth to which the lancing electrode is inserted will depend on the variation in length between it and that of the outer electrode or by some other means associated with sensor unit 10 for limiting the insertion depth. More particularly, depending on the relative lengths of the inner electrode and the outer electrode of sensor device 10, the area of skin covered by sensor system, may bulge into the reaction zone spacing, thereby causing the inner lancing electrode to penetrate the skin with minimal applied pressure. As such, the distal edge of the outer electrode functions as a pressure "ring" or surface.

Upon insertion of the inner electrode into the patient's skin, an amount (i.e., a sample) of biological fluid emerges from or flows out of from the puncture site and is wicked into the reaction chamber by means of a capillary action. Once in the reaction zone, the targeted analyte chemically reacts with the selected reagent(s) to form electroactive products or species, which can be measured directly, or indirectly through the action of a mediator. The resulting products or species will be either oxidized or reduced at the surface of the working electrode, generating a current signal. The current signal is proportional to the concentration of the target analyte in the biological fluid.

An electrical input signal, such as a constant potential, is provided by the control unit 52 to the reference electrode and the working electrode. The current output generated by the resulting products or species, is then conducted to control unit 52 by the working electrode. A software algorithm programmed within control unit 52 then automatically determines the differential between the output and reference signals, derives the concentration of analyte in the sample from this differential value, and then derives the corresponding concentration level of the selected analyte in the patient's blood. Any or all of these values may be displayed by display means or screen 58.

A device such as control unit 52 which automatically calculates and determines the concentration of a selected analyte in a biological sample and/or in the patient's system, such that a user need only insert skin-piercing member of the subject invention into the patient's skin and then read the final analyte concentration result from a display of the device, is further described in U.S. Pat. No. 6,193,873 entitled "Sample Detection to Initiate Timing of an Electrochemical Assay," the disclosure of which is herein incorporated by reference.

Kits

Also provided by the subject invention are kits for use in practicing the subject methods. The kits of the subject invention include at least one subject sensor device. The kits may also include a reusable or disposable control unit that may be used with reusable or disposable sensor devices of the kit or from other kits of the subject invention. These kits may include an array of sensor devices with lancing members having the same or different lengths. Certain kits may include various sensors each containing the same or different reagents. Also, more than one reagent may be provided within a single array, wherein one or more of the sensor devices are provided with a first reagent for testing a first target analyte and one or more other sensor devices are provided with other reagents for testing other targeted analytes. Finally, the kits preferably include instructions for using the subject sensors in the determination of an analyte concentration in a physiological sample. These instructions may be present on one or more of the packaging, a label insert, or containers present in the kits, and the like.

It is evident from the above description that the subject inventions are easy to use and can provide for analyte testing with minimal or no pain and blood. As such, the subject invention represents a significant contribution to the field.

The subject invention is shown and described herein in what is considered to be the most practical, and preferred embodiments. It is recognized, however, that departures may be made there from, which are within the scope of the invention, and that obvious modifications will occur to one skilled in the art upon reading this disclosure.

Although the present invention is useful for many applications, the sampling of various biological fluids and the detection of many types of constituents, the invention has been described primarily in the context of the detection of analytes in interstitial fluids, and as being particularly useful for the detection of glucose in interstitial fluid. Thus, the specific devices and methods disclosed and the applications, biological fluids and constituents discussed herein are considered to be illustrative and not restrictive. Modifications that come within the meaning and range of equivalents of the disclosed concepts, such as those that would readily occur to one skilled in the relevant art, are intended to be included within the scope of the appended claims.

What is claimed is:

1. A device for sampling a biological fluid and measuring a target constituent within the biological fluid, comprising:

an outer electrode having a length;

an inner electrode having a length and positioned within and spaced apart from the outer electrode;

an open chamber between said inner and outer electrodes, the open chamber extending substantially the length of the outer electrode and of the inner electrode and having a volume sufficient to provide a capillary force on biological fluid in contact with the open chamber.

2. An electrochemical cell for use in sampling biological fluid and measuring an analyte therein, the cell comprising:

a first electrode; and a second electrode positioned concentrically within and spaced-apart from the first electrode and comprising a distal end configured to pierce a skin surface, wherein the first and second electrodes have the same length.

3. A system for sampling biological fluid from the skin of a patient and measuring a target constituent within the biological fluid, the system comprising:

(a) an array of electrochemical cells wherein each cell comprises a first electrode and a second electrode spaced-apart from each other, wherein the first electrode is positioned concentrically about the second electrode and the second electrode comprises a distal end configured to pierce a skin surface; and (b) a control unit in electrical communication with the array, comprising:

(1) means for sending an electrical reference signal to each of the first electrodes and for receiving an electrical output signal from each of the second electrodes, and (2) a software algorithm which automatically calculates and determines the concentration of the target constituent in the biological sample upon receipt of the electrical output signal.

4. A device for sampling a biological fluid and measuring a target constituent within the biological fluid, comprising:

an inner electrode having a proximal end;

an outer electrode having a cylindrical configuration comprising a proximal end, and an open distal end;

an annular vacant space between said inner and outer electrodes;

an insulating material positioned between a portion of the proximal ends of the inner and outer electrodes; and a skin-lancing member extending from the distal end of the inner electrode.

5. The device of claim 4 wherein the facing surfaces of the inner and outer electrodes and the insulating material defines a reaction chamber having dimensions sufficient to exert a capillary force on fluid present at the distal ends of the electrodes.

6. The device of claim 4 further comprising a base from which the electrodes extend.

7. The device of claim 4 further comprising a signal producing and receiving means in electrical communication with the electrodes.

8. A system for sampling biological fluid from the skin of a patient and measuring a target constituent within the biological fluid, the system comprising:

(a) an electrochemical cell comprising a first electrode and a second electrode spaced-apart from each other, wherein the first electrode is positioned concentrically about the second electrode and the second electrode comprises a distal end configured to pierce a skin surface, wherein at least a portion of the space between the electrodes is vacant; and (b) a control unit in electrical communication with the electrochemical cell, comprising:

(1) means for sending an electrical reference signal to the first electrode and for receiving an electrical output signal from the second electrode, and (2) a software algorithm which automatically calculates and determines the concentration of the target constituent in the biological sample upon receipt of the electrical output signal.

9. The system according to claim 8 further comprising a display unit in electrical communication with the control unit for displaying information in the form of electrical signals received from the control unit related to the sampling of the biological fluid and the measuring of the target constituent.

10. The system according to claim 8 further comprising a housing and a support means wherein the control unit is housed within the housing and the at least one electrochemical cell is mounted to the support means.

11. The system of claim 8 comprising an array of electrochemical cells.

12. A method for testing a biological fluid within the skin of a patient and for determining the concentration of a target constituent contained therein, the method comprising the steps of:

providing an electrochemical cell comprising a concentrically spaced-apart inner and outer electrodes and a reaction chamber therebetween and extending along a substantial portion thereof; wherein the inner electrode comprises a lancing member;

inserting the lancing member into the skin to a selected depth wherein biological fluid exits from the skin;

transferring a sample of biological fluid into the reaction chamber;

providing a first electrical signal to the electrochemical cell; and receiving a second electrical signal generated by the electrochemical cell, wherein the second electrical signal is representative of the concentration the constituent in the sample.

13. A method according to claim 12 wherein the step of transferring comprises exerting a capillary force on the sampled biological fluid.

14. A method according to claim 12 wherein the steps of providing a first electrical signal and receiving a second electrical signal is performed by a control unit in electrical communication with the electrochemical cell.

15. A method according to claim 12 wherein the selected depth is no greater than the dermis.

16. The method according to claim 15 wherein the selected depth is no greater than the viable epidermis.

17. The method according to claim 16 wherein the selected depth is no greater than the stratum corneum.

18. A method according to claim 16 further comprising the step of deriving the concentration of the constituent in the patient's biological fluid from the second electrical signal.

19. The method according to claim 18 further comprising the step of displaying a numerical value representative of the concentration of the constituent in the patient's biological fluid.

20. The method according to claim 18 wherein the step of deriving comprises using a software algorithm.

21. An electrochemical cell for use in sampling biological fluid and measuring an analyte therein, the cell comprising:

a first electrode having a length; and a second electrode having a length and a distal end configured to pierce a skin surface, the second electrode positioned concentrically within and spaced apart form the first electrode wherein at least a portion of the space is vacant.

22. The electrochemical cell of claim 21 wherein the second electrode has an elongated configuration having a length that is co-axial with the first electrode.

23. The electrochemical cell of claim 21 further comprising an insulator positioned within at least a portion of the space between the first and second electrodes.

24. The electrochemical cell of claim 21 wherein the first and second electrodes have the same length.

25. The electrochemical cell of claim 21 wherein the biological fluid is interstitial fluid or blood and the analyte is glucose.

26. The electrochemical cell according to claim 21 further comprising a reagent material in contact on a surface of at least one of the electrodes wherein said surface is facing the other electrode.

27. The electrochemical cell of claim 21 wherein the vacant space defines a volume sufficient to provide a capillary force on biological fluid in contact with the vacant space.

28. The electrochemical cell of claim 21 wherein the vacant space defines a volume in the range from about 0.1 $\mu l$ to about 2 $\mu l$.

29. The electrochemical cell of claim 21 wherein a substantial portion of the space between the electrodes is vacant.

30. The electrochemical cell of claim 21 wherein the second electrode has a diameter about 500 $\mu m$ or less.

31. The electrochemical cell of claim 21 wherein the second electrode has a penetration length extending no deeper than the dermis layer when fully penetrated into the skin.

32. The electrochemical cell of claim 21 wherein the first and second electrodes have different lengths.

33. The electrochemical cell of claim 32 wherein the first electrode is shorter than the second electrode.

34. The electrochemical cell of claim 32 wherein the first electrode is longer than the second electrode.

35. The electrochemical cell according to claim 21 wherein the second electrode has a penetration length no deeper than the dermis.

36. The electrochemical cell according to claim 35 wherein the second electrode has a penetration length no deeper than the epidermis.

37. The electrochemical cell according to claim 21 wherein the first electrode comprises a skin-contacting surface at a distal end for exerting pressure on the skin surface adjacent the distal end of the second electrode.

38. The electrochemical cell according to claim 37 wherein the skin-contacting surface has a ring configuration.

39. A kit for sampling a biological fluid from the skin of a patient and for measuring the concentration of a constituent within the sampled biological fluid, the kit comprising:
at least one electrochemical cell according to claim 1.

40. The kit according to claim 39 further comprising one or more reagents for facilitating the measurement of one or more constituents within the sampled biological fluid.

41. The kit according to claim 39 comprising a plurality of electrochemical cells and a support member wherein the plurality of electrochemical cells are arranged in an array on the support member.

42. The kit according to claim 41 wherein the inner electrodes of the plurality of electrochemical cells have varying penetration lengths.

43. The electrochemical cell of claim 21 wherein the first electrode comprises a continuous wall configuration having an open distal end and a distal edge.

44. The electrochemical cell of claim 43 wherein the continuous wall comprises a cylindrical configuration and the distal edge define a skin-contacting surface.

45. The electrochemical cell of claim 43 wherein the space between the electrodes has a thickness sufficient to exert a capillary force on fluid present at the open distal end of the first electrode.

46. The electrochemical cell of claim 45 wherein the thickness is in the range from about 250 to 1500 $\mu$m.

* * * * *